United States Patent [19]

Cleary

[11] Patent Number: 4,854,864
[45] Date of Patent: Aug. 8, 1989

[54] ORTHODONTIC BRACKET AND PALATAL BAR SYSTEM

[75] Inventor: James D. Cleary, Glendora, Calif.

[73] Assignee: Unitek Corporation, Monrovia, Calif.

[21] Appl. No.: 118,794

[22] Filed: Nov. 9, 1987

[51] Int. Cl.$^4$ .............................................. A61C 7/00
[52] U.S. Cl. ........................................... 433/7; 433/8
[58] Field of Search ...................... 437/7, 8, 9, 10, 11, 437/12, 13, 14, 15, 16

[56] References Cited

U.S. PATENT DOCUMENTS

| | | |
|---|---|---|
| 1,487,698 | 7/1921 | Aderer . |
| 1,905,877 | 9/1931 | Aderer . |
| 1,919,762 | 9/1931 | Aderer . |
| 2,032,282 | 10/1932 | Irish . |
| 3,162,948 | 5/1962 | Gerber . |
| 3,792,529 | 2/1974 | Goshgarian . |
| 4,028,808 | 6/1977 | Schwartz . |
| 4,144,643 | 3/1979 | Krygler . |
| 4,200,979 | 5/1980 | Wallshein . |
| 4,239,487 | 12/1980 | Murdock . |
| 4,354,832 | 10/1982 | Wallshein . |
| 4,392,826 | 7/1983 | Goshgarian . |
| 4,408,989 | 10/1983 | Cleary . |
| 4,416,626 | 11/1983 | Bellavia . |
| 4,433,956 | 2/1984 | Witzig . |
| 4,482,318 | 11/1984 | Forster . |
| 4,571,177 | 2/1986 | Dahan . |
| 4,592,725 | 6/1986 | Goshgrian . |

*Primary Examiner*—Robert Peshock
*Attorney, Agent, or Firm*—Christie, Parker & Hale

[57] ABSTRACT

An orthodontic bracket and palatal bar system for lingual placement in the maxillary dental arch. The bracket provides a generally vertical socket to receive a pin on the adjacent end of the palatal bar by upward movement of the bar within the mouth. The bar has an antirotation link which seats in a mating bracket slot, and the bracket includes a separate rectangular slot to receive an edgewise arch wire.

13 Claims, 4 Drawing Sheets

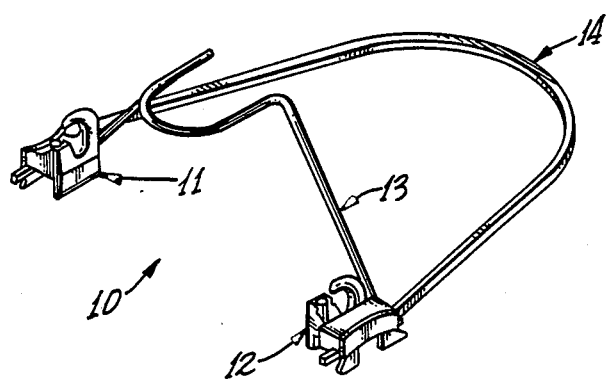

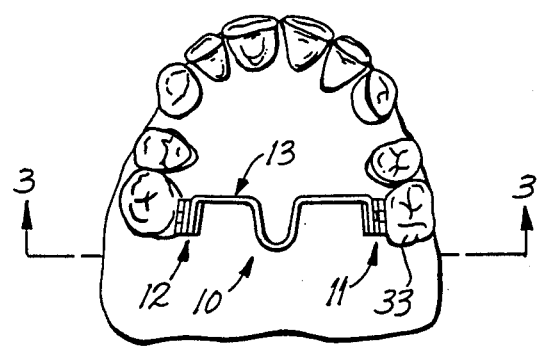
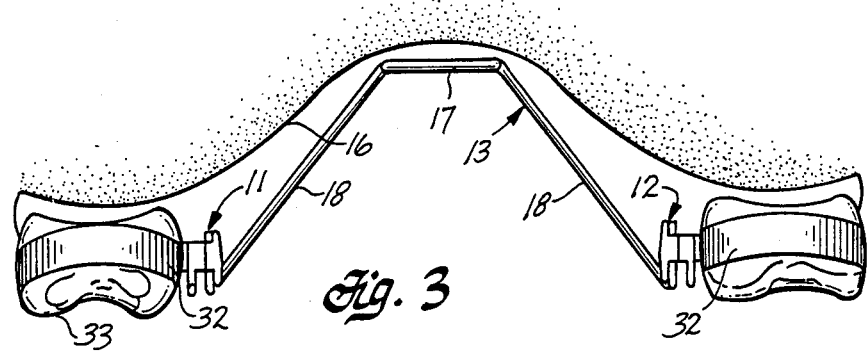
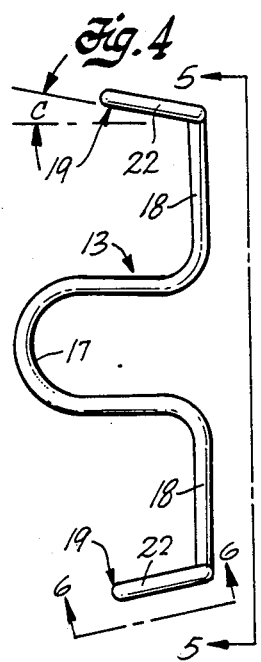
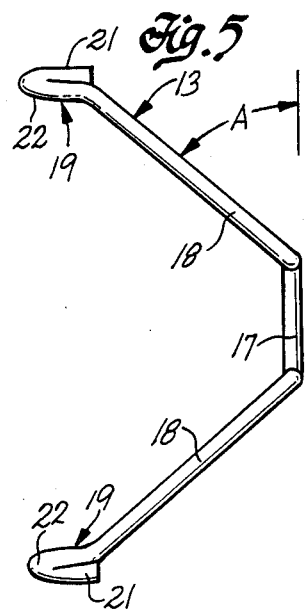
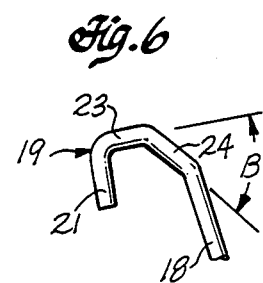

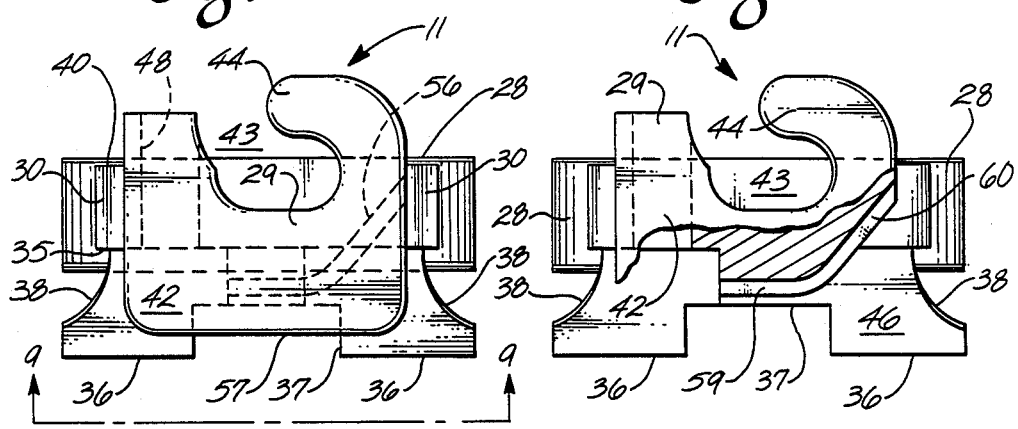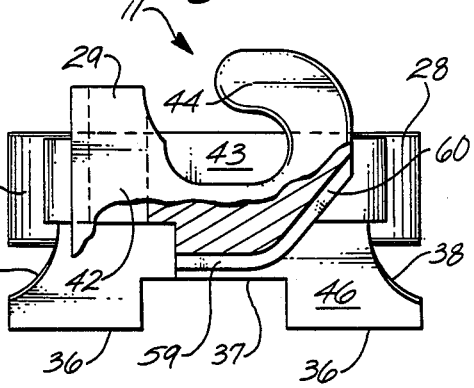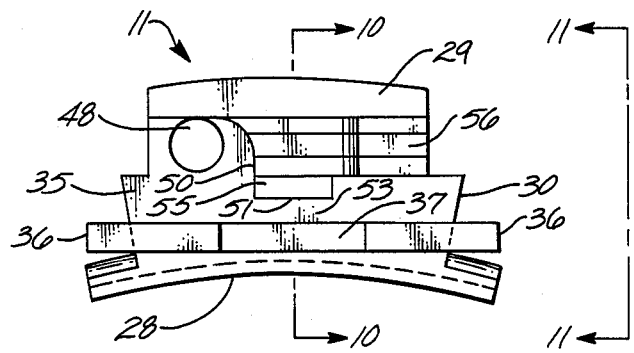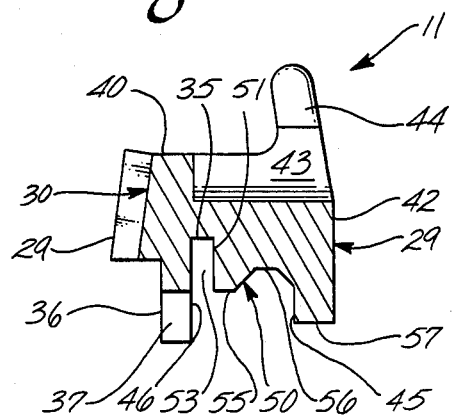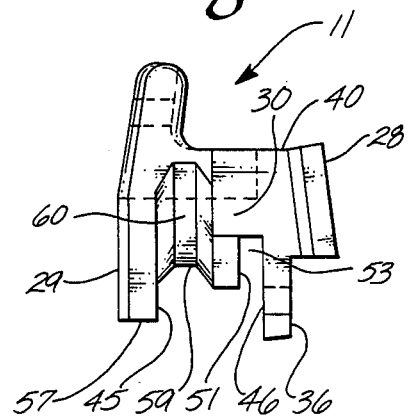

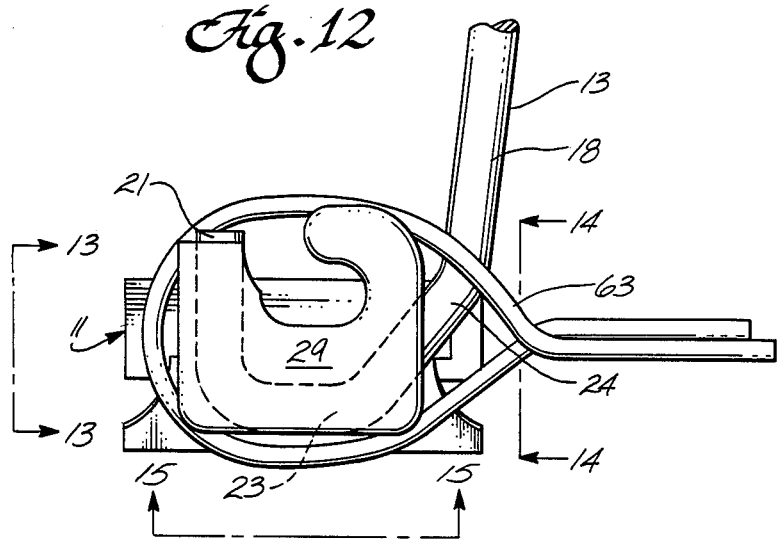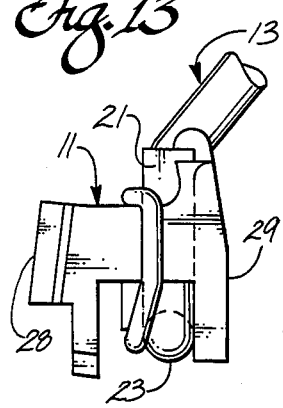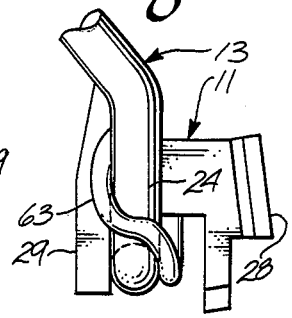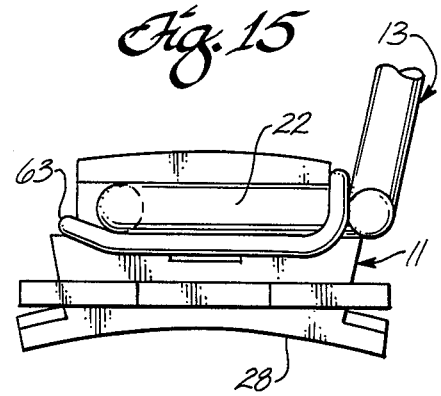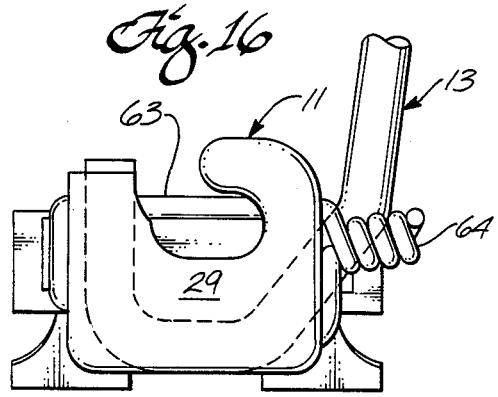

ORTHODONTIC BRACKET AND PALATAL BAR SYSTEM

BACKGROUND OF THE INVENTION

A palatal bar is a known orthodontic appliance which is used during initial treatment to reposition misaligned molar teeth by application of rotating, tipping or torquing forces. An equally important application is in stabilizing and maintaining molar teeth in an orthodontically correct position while the molars are used as force-reaction anchors during application of corrective forces for repositioning of other teeth (incisors, cuspids and bicuspids) in the patient's mouth.

The palatal bar is used in the upper or maxillary dental arch, and is positioned within the arch to be mounted on and extend between the left and right upper molars. The specific teeth are typically the first permanent molars which erupt years before the second permanent molars, but the palatal bar can be used on any reasonably erupted pair of molars. The bar has an upwardly arched central or bridging portion which generally follows the curvature of the hard palate to avoid tongue interference. The central bridging portion is integrally connected between palatal-bar terminal ends which are engaged in brackets (typically welded to tooth-encircling metal bands) mounted on the lingual or tongue-facing surface of the molars.

The application and general function of palatal bars is known, and is described in greater detail in my U.S. Pat. No. 4,408,989, and in, for example, U.S. Pat. Nos. 3,792,529 and 4,582,725. For brevity, these general concepts will not be here restated, and the disclosures of the aforementioned patents are incorporated herein by reference.

An important and growing orthodontic method is so-called lingual treatment where orthodontic brackets and associated arch wires are mounted on the inner or lingual surfaces of the teeth. This technique is especially appealing to teenage or adult patients, because the brackets and wires are largely concealed by the teeth and are not plainly visible during smiling. The palatal bar is inherently a lingual device and is a useful component in carrying out a lingual treatment program. The bar, however, is also useful when applied in a treatment program using conventional brackets and arch wires on the outer or buccolabial tooth faces.

Two problems, both overcome by the present invention, are presented by known palatal bars and associated brackets used in lingual treatment. First, the molar brackets to which the palatal-bar ends are secured should also receive a lingual arch wire which spans the upper dental arch and applies corrective force to teeth anterior of the molars. It is necessary to remove and adjust (or replace) the arch wire as treatment progresses, and prior-art brackets typically require painstaking and time-consuming removal and replacement of the palatal bar to gain access to the arch wire.

The second problem is that known bars and brackets are engaged by movement of the bar ends in a mesiodistal direction (generally parallel to the occlusal plane defined by the exposed tooth ends, and in the direction of the adjacent dental arch) into some kind of mating socket or slot in each bracket. This kind of movement is made difficult by the small available space within the upper dental arch, and by interference of the disengaged palatal bar with lingual brackets or similar appliances on teeth (especially bicuspids) anterior of the molars.

The bracket and palatal bar system of this invention overcomes both of these problems. The bracket provides separate slots or sockets for the palatal bar and arch wire, and is arranged so these components are separately ligated, and are separately removable without disturbing the other component. The bracket and bar are also configured so the bar terminal ends can be engaged and locked to the molar brackets by upward (rather than forward or rearward) movement of the bar within the upper arch beneath the palate, thereby avoiding interference with appliances already installed on teeth anterior to the molars.

SUMMARY OF THE INVENTION

The palatal bar of this new system is characterized by an upwardly arched center section which terminates at opposite ends in hooks, each hook ending in an upwardly extending pin oriented on an occlusogingival axis when the bar is installed. An antirotation link extends between each pin and a respective end of the center section.

The bracket of the system is configured for conventional tooth-band mounting on a molar tooth, and includes an upwardly extending socket positioned to receive the palatal-bar hook pin when the bar is moved upwardly in the mouth toward the palate. The bracket has a slot extending laterally from the socket to receive the antirotation link, and thereby to prevent lateral movement of the link and rotation of the seated pin. The bracket has a separate slot to receive an edgewise arch wire, and separate ligation paths are provided in the bracket for the arch wire and palatal bar.

BRIEF DESCRIPTION OF THE DRAWINGS

FIG. 1 is a pictorial view of a palatal bar engaged with a pair of molar lingual brackets, and an arch wire engaged with the brackets;

FIG. 2 is a bottom or occlusal diagrammatic view of an upper dental arch with the palatal bar and brackets mounted on first upper molars;

FIG. 3 is a rear elevation on line 3—3 of FIG. 2 showing only the molars, brackets and palatal bar;

FIG. 4 is a bottom or occlusal view of the palatal

FIG. 5 is a view on line 5—5 of FIG. 4;

FIG. 6 is a view on line 6—6 of FIG. 4;

FIG. 7 is an elevation of the front or lingual surface of the upper left molar bracket (the upper right molar bracket being a mirror image);

FIG. 8 is a view similar to FIG. 7, but partly broken away to show a ledge to support the palatal bar;

FIG. 9 is a bottom or occlusal view of the bracket on line 9—9 of FIG. 7;

FIG. 10 is a sectional view on line 10—10 of FIG. 9;

FIG. 11 is an end view on line 11—11 of FIG. 9 showing a mesial end of the bracket;

FIG. 12 is a front elevation of the assembled bar and bracket in readiness for ligation;

FIG. 13 is a view on line 13—13 of FIG. 12;

FIG. 14 is a view on line 14—14 of FIG. 12;

FIG. 15 is a view on line 15—15 of FIG. 12; and

FIG. 16 is a view similar to FIG. 12 showing an installed ligature wire.

DESCRIPTION OF THE PREFERRED EMBODIMENT

FIG. 1 shows in pictorial form a palatal bar and bracket system 10 according to the invention. The system includes an upper left molar bracket 11, an upper right molar bracket 12, and a palatal bar 13 having ends engaged With the brackets. The brackets also provide slots (described below) to receive a conventional round or edgewise (rectangular cross section) lingual arch wire 14 which extends around the upper dental arch for engagement with other brackets (not shown) mounted on the lingual or inner tongue-facing surfaces of upper arch teeth which are anterior of the molars. FIGS. 2-3 show the system as installed, and these views are discussed below after describing the system components.

Referring to FIGS. 1 and 3-6, palatal bar 13 is integrally formed of stainless-steel wire (round wire of 0.036 cross-sectional diameter is typical and preferred) to extend between the molars in an upwardly arched shape which generally follows the contour of the palate 16 (FIG. 3). The bar has a central U-shaped bight or loop 17 extending rearwardly in the mouth and generally parallel to the palate. The loop ends curve smoothly into a pair of oppositely and downwardly angled arms 18 (angle A in FIG. 5 is typically about 50 degrees), and the lower end of each arm is integrally joined to a hook 19.

Each hook 19 terminates in an occlusogingivally extending pin 21 which is integrally joined to an antirotation link 22 having first and second portions 23 and 24. The hook is flat (i.e., the longitudinal axes of pin 21 and link portions 23 and 24 are coplanar), and first portion 23 extends perpendicularly and mesially from the gingivally directed pin. Link 22 is bent to define an angle of about 50 degrees (angle B in FIG. 6) between portions 23 and 24, and portion 24 is integrally joined with associated arm 18. As shown in FIG. 4, the hooks are slightly outwardly splayed at an angle C (typically about 11 degrees) to conform to the orientation of the molar lingual surfaces in the dental arch.

Upper left molar bracket 11 (a mirror image of, but otherwise identical to, upper right molar bracket 12) is shown in detail in FIGS. 7-11. The bracket is preferably a machined block of stainless steel, but can also be integrally cast. The shape of the bracket is somewhat complex, but it is most easily envisioned as includig a buccal (cheek facing) or inner surface forming a mounting base 28, a lingual or outer surface forming a lingual plate 29, and a body 30 integrally joined to and extending between base 28 and plate 29.

Mounting base 28 is a conventional rectangular welding flange which is slightly concave to mate with the convex surface of a stainless-steel tooth band 32 (FIG. 3), which is fitted over and cemented to an upper left molar 33. The mounting-base flange and tooth band are secured together by conventional spot welding or brazing.

Bracket body 30 has a lower or occlusal surface 35 which is substantially flat, and a pair of mesiodistally spaced-apart tie wings 36 extend downwardly or occlusally from the generally buccal side of surface 35. The tie wings are spaced slightly lingually from base 28 and are separated by a notch 37. The tie wings define oppositely facing cleat-like recesses 38 for retention of a ligature as described below.

The lingual end of body 30 is integrally joined to lingual plate 29 which is enlarged occlusogingivally to extend below body occlusal surface 35, and above a generally flat bracket-body upper or gingival surface 40 which is substantially parallel to surface 35. Plate 29 has a lingual surface 42 which is slightly convex mesiodistally (FIG. 9), and an opening 43 is formed through the upper part of the plate and into the bracket body to define a hook 44 for anchorage of an elastic band (not shown) or other auxiliary intraoral device.

Lingual plate 29 has an inner (buccal) lower surface 45 which is generally flat and parallel to a facing lingual surface 46 of tie wings 36. The upper part of plate 29 which forms hook 44 is angled slightly (about 10 degrees) buccally (toward tooth band 32) to minimize lingual protrusion of the hook as shown in FIGS. 10 and 11.

A cylindrical socket 48 (FIGS. 7 and 9) extends occlusogingivally (generally vertically, and with an axis perpendicular to body occlusal surface 35) through body 30 adjacent lingual plate 39 and slightly spaced from the distal end of bracket body 30. The socket has an inside diameter and length selected to permit pin 21 of the palatal bar to be fully inserted therein with about 0.001-0.002 inch diametrical clearance. For machining convenience, socket 48 is preferably a bore entirely through the bracket body, but the gingival end of the socket can be closed if desired.

An integrally formed ledge 50 extends buccally from the buccal surface of lingual plate 29, and occlusally or downwardly from the central part of surface 35 of the bracket body. The ledge is slightly mesially spaced from socket 48. Ledge 50 has an occlusogingivally extending buccal surface 51, which is spaced from and parallel to lingual surface 46 of tie wings 36 to define a downwardly or occlusally opening and mesiodistally extending arch-wire slot 53 for receiving a conventional rectangular-cross-section lingual arch wire (not shown).

Ledge 50 has a flat undersurface 55 extending lingually from the open end of arch-wire slot 53. An occlusogingivally extending palatal-bar groove or slot 56 extends upwardly in ledge 50 between undersurface 55 and an occlusal undersurface 57 of lingual plate 29. Slot 56 is shown as having a flat-bottom inverted V-shape in cross section, but can also be upwardly semicircular in cross section. In either case, the slot is dimensioned to receive antirotation link 22 of palatal-bar hook 19.

As best seen in FIGS. 7-9 and 11, slot 56 has a first-level portion 59 which extends generally parallel to body surface 35, and a second sloping portion 60 extending mesially and gingivally into bracket body 30 from ledge 50. The angulation of first and second portions 59 and 60 matches the angulation of palatal-bar antirotation link portions 23 and 24. Slot 56 thus provides a seat for the entire antirotation link of palatal-bar hook 19 to prevent rotation of the installed hook about the longitudinal axis of hook pin 21.

In use, brackets 11 and 12 are secured by tooth bands 32 to respective molar teeth at opposite ends of the dental arch as shown in FIGS. 2 and 3. The orthodontist then places any desired activating bends in loop 17 and arms 18 of the palatal bar to apply corrective forces to the molars. Alternatively, the palatal bar can be shaped in a zero-force configuration as a stabilizing device to resist unwanted movement of the molars. In either case, bending of the palatal bar is confined to loop 17 and arms 18 to avoid upsetting the coplanarity and preset angulation of hook pin 21 and antirotation link 22 which are configured to fit smoothly and easily into bracket socket 48 and palatal-bar slot 56 respectively.

The palatal bar is then inserted in the patient's mouth, with pins 21 immediately below and aligned with sockets 48 of brackets 11 and 12. The bar is next raised to fit pins 21 fully into sockets 48, and thereby to seat antirotation links 22 in respective palatal-bar slots 56 of the brackets. The pin-socket connection anchors the palatal bar, and rotation of the pin within the socket (which would interfere with proper functioning of the bar) is revented by seating of the antirotation links which are confined against lateral movement by the sidewalls of palatal-bar slots 56.

Installation of the palatal bar is completed by ligating each hook end of the bar to the respective bracket. A recommended ligation procedure is shown in FIGS. 12-16, and this technique provides secure anchorage of the bar to the bracket without occluding or interfering with arch-wire slot 53.

FIG. 12 shows the starting position of a ligature wire 63 (of the conventional soft stainless-steel type) loosely looped around the buccal side of lingual plate 29. FIGS. 13-15 show the preferred positions of the tightened ligature wire, and FIG. 16 illustrates the completed installation with the trimmed ligature-wire ends terminating in a twisted pigtail 64 (which can be bent rearwardly to seat behind lingual plate 29 on the gingival side of the bracket).

Importantly, arch-wire slot 53 remains clear and open after installation of the palatal-bar ligature wire, and an arch wire can be slipped into this slot and independently ligated in place (typically using an O-ring-like elastic ligature looped under the arch wire and anchored between tie wings 36 and the upper or gingival surface of the bracket). Removal and replacement of either the arch wire or the palatal bar can be accomplished during intermediate-phase treatment adjustments without disturbing the other component, resulting in a significant time-saving for orthodontist and patient.

There has been described a novel palatal bar and bracket system which enables simplified coupling of bar and bracket by bar movement in only an occlusogingival direction which avoids interference with other lingual appliances installed in the dental arch. The bracket is further characterized by independent anchorage and ligation paths for the palatal bar and a separate arch wire which is often needed in lingual treatment programs.

What is claimed is:

1. A palatal bar and bracket system, comprising:
a palatal bar having an upwardly arched center section, and a pair of hooks integrally joined to lower opposite ends of the center section, each hook terminating in an upwardly extending pin with and occlusional axis when the bar is installed in a patient's mouth, each hook further having an antirotation link extending laterally from an occlusal end of the pin; and
an orthodontic bracket, the bracket defining an upwardly extending socket with a generally occlusogingival axis when the bracket is mounted on a maxillary tooth, the bracket further defining a first slot extending laterally from the socket to receive the antirotation link when the palatal bar is raised in the mouth to said the hook pin in the bracket socket, rotation of the hook pin with resect to the socket and lateral movement of the antirotation link being prevented by seating of the antirotation link in the first slot.

2. The system defined in claim 1 wherein the first slot is on an occlusal side of the bracket.

3. The system defined in claim 2 wherein the bracket defines a second occlusally opening slot spaced from the first slot and configured to receive an orthodontic arch wire.

4. The system defined in claim 3 wherein the bracket includes an occlusally extending ledge which separates the first and second slots.

5. The system defined in claim 4 wherein the bracket defines a lingual plate further forming a hook for anchorage of an auxiliary appliance.

6. The system defined in claim 5 wherein the bracket defines at least one tie wing adjacent the second slot to anchor an arch-wire ligature.

7. An orthodontic palatal bar for intraoral placement between left and right maxillary molar teeth, the bar comprising an upwardly arched center section with a central and distally extending loop which is generally parallel to the oral palate when the bar is installed, the loop being integrally joined with a pair of arms which extend downwardly and buccally toward the respective molar teeth, the lower end of each arm being integrally joined to a respective hook, each hook terminating in an upwardly extending pin, the pin being integrally connected to the respective arm by a mesiodistally extending link.

8. The bar defined in claim 7 wherein the hook link has a first portion extending generally perpendicularly and mesially from the pin, and a second portion extending upwardly and mesially from the first portion to join the respective arm.

9. The bar defined in claim 8 wherein the pin and first and second link portions are coplanar.

10. An orthodontic bracket, comprising a base adapted for attachment to a tooth, a body extending from the base and defining a pair of mesiodistallly oriented spaced-apart first and second fixed slots, the body further defining an occlusogingivally extending and occlusally open socket adjacent one end of the first slot, the second slot being adjacent the base and configured to receive an edgewise arch wire.

11. The bracket defined in claim 10 wherein the first and second slots are open occlusally, the body defining an occlusally extending ledge between and separating the first and second slots.

12. The bracket defined in claim 11 which further includes a plate integrally joined to the body and spaced from the base, the plate forming a side surface of the first slot and defining a hook.

13. The bracket defined in claim 12 wherein the bracket includes a pair of tie wings extending from the body adjacent the second slot.

* * * * *

UNITED STATES PATENT AND TRADEMARK OFFICE
CERTIFICATE OF CORRECTION

PATENT NO. : 4,854,864

DATED : August 8, 1989

INVENTOR(S) : James D. Cleary

It is certified that error appears in the above-identified patent and that said Letters Patent is hereby corrected as shown below:

Col. 5, line 9, "revented" should read -- prevented --.

Col. 5, line 52, "and" should read -- an --.

Col. 6, line 2, "said" should read -- seat --.

Col. 6, line 3, "resect" should read -- respect --.

Signed and Sealed this

Eleventh Day of December, 1990

*Attest:*

HARRY F. MANBECK, JR.

*Attesting Officer*  *Commissioner of Patents and Trademarks*